US010624548B2

(12) United States Patent
Keisler

(10) Patent No.: US 10,624,548 B2
(45) Date of Patent: Apr. 21, 2020

(54) ELECTRODE ASSEMBLY WITH THREAD ELECTRODE

(71) Applicant: Rhythmlink International, LLC, Columbia, SC (US)

(72) Inventor: Gerald Keisler, Lexington, SC (US)

(73) Assignee: Rhythmlink International, LLC, Columbia, SC (US)

( * ) Notice: Subject to any disclaimer, the term of this patent is extended or adjusted under 35 U.S.C. 154(b) by 360 days.

(21) Appl. No.: 15/696,850

(22) Filed: Sep. 6, 2017

(65) Prior Publication Data

US 2018/0353132 A1 Dec. 13, 2018

Related U.S. Application Data

(60) Provisional application No. 62/385,434, filed on Sep. 9, 2016.

(51) Int. Cl.
| | |
|---|---|
| *A61B 5/04* | (2006.01) |
| *A61B 5/0478* | (2006.01) |
| *A61B 5/00* | (2006.01) |
| *A61B 17/34* | (2006.01) |
| *A61B 5/0492* | (2006.01) |

(52) U.S. Cl.
CPC ........ *A61B 5/04001* (2013.01); *A61B 5/0478* (2013.01); *A61B 5/0492* (2013.01); *A61B 5/4058* (2013.01); *A61B 5/6849* (2013.01); *A61B 17/3496* (2013.01); *A61B 17/3468* (2013.01); *A61B 2560/063* (2013.01); *A61B 2562/00* (2013.01); *A61B 2562/16* (2013.01)

(58) Field of Classification Search
CPC .. A61B 5/04001; A61B 5/0478; A61B 5/0492
USPC .......................................................... 600/383
See application file for complete search history.

(56) References Cited

U.S. PATENT DOCUMENTS

| | | | |
|---|---|---|---|
| 4,417,581 A * | 11/1983 | Dawson | A61B 5/0496 600/383 |
| 5,645,076 A | 7/1997 | Yoon | |
| 6,547,762 B1 | 4/2003 | Botich et al. | |
| 6,652,519 B2 | 11/2003 | Maltese | |
| 6,912,424 B2 * | 6/2005 | Bishay | A61N 1/0551 607/115 |
| 8,855,736 B2 | 10/2014 | Jaffe et al. | |
| 2005/0085807 A1 | 4/2005 | Venturelli | |
| 2006/0161058 A1 | 7/2006 | Ives et al. | |

(Continued)

FOREIGN PATENT DOCUMENTS

WO 2016126340 A2 8/2016

*Primary Examiner* — Lee S Cohen
(74) *Attorney, Agent, or Firm* — Nexsen Pruet, LLC; Michael A. Mann

(57) ABSTRACT

An electrode assembly includes a needle and a conductive thread electrode carried in a slot on the surface of the needle. The needle pushes the thread electrode into the body and leaves it in place when the needle is removed. The needle is secured in a housing in a retracted position and moved to an extended position by a latch. In the extended position, one end of the needle remains in the housing and the other end extends from the housing. The needle is attached to a spring inside the housing and is moved by the latch against the urging of the spring to the extended position and locked in place. A protective cover is applied over the needle while extended and removed to insert the needle into the body of a patient.

14 Claims, 6 Drawing Sheets

(56) References Cited

U.S. PATENT DOCUMENTS

| | | |
|---|---|---|
| 2008/0127978 A1 | 6/2008 | Rubin et al. |
| 2012/0296230 A1* | 11/2012 | Davis ................. A61B 5/04001 600/546 |
| 2015/0141786 A1* | 5/2015 | Durand .............. A61B 5/04001 600/377 |
| 2016/0096015 A1 | 4/2016 | Gehl et al. |
| 2017/0049991 A1 | 2/2017 | Avneri et al. |
| 2017/0182312 A1* | 6/2017 | Durand ................ A61N 1/0558 |

* cited by examiner

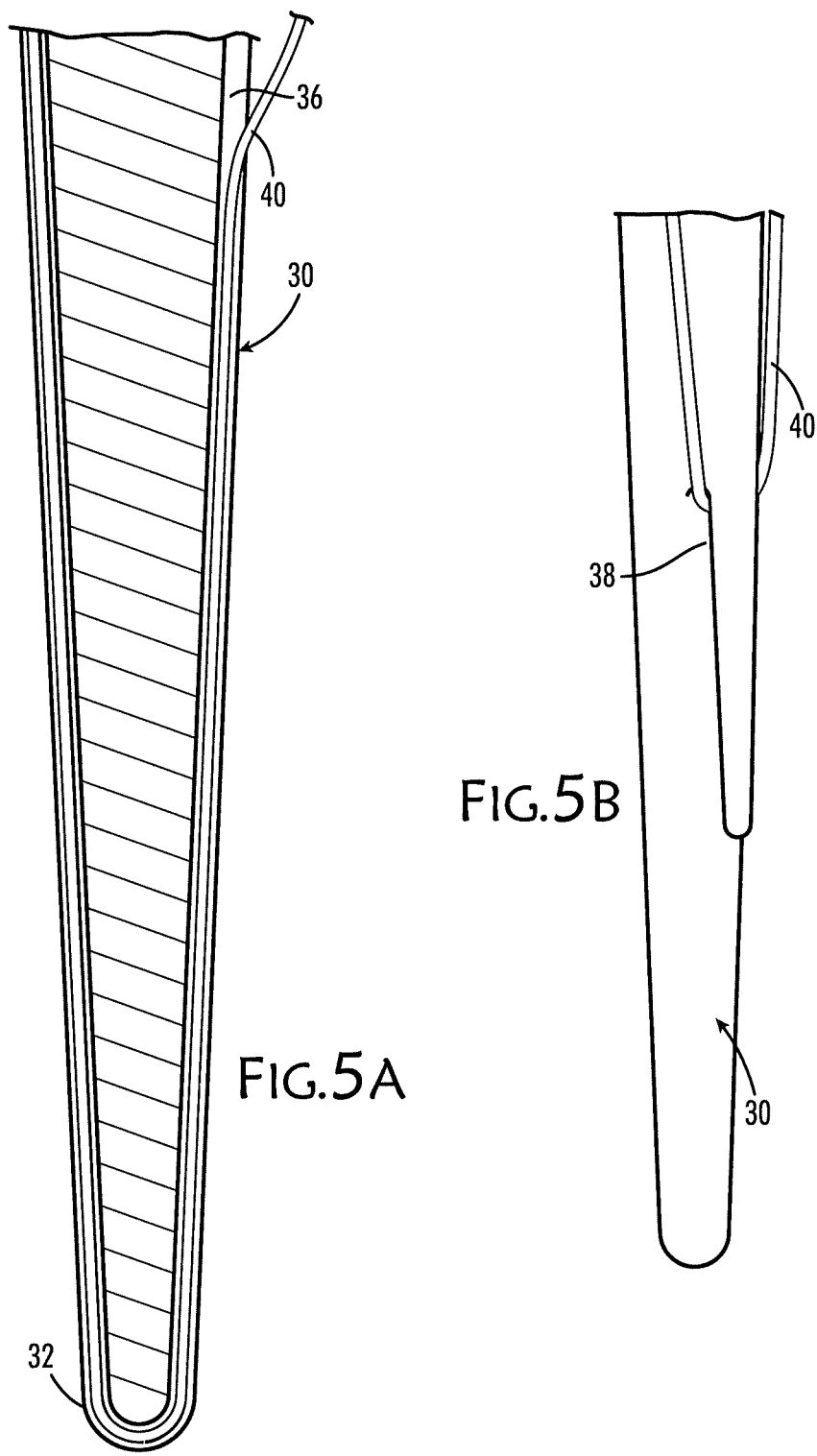

US 10,624,548 B2

ELECTRODE ASSEMBLY WITH THREAD ELECTRODE

TECHNOLOGICAL FIELD

The present disclosure is related in general to electrodes for neurological monitoring and the devices used for deploying such electrodes.

Neurological monitoring is performed to detect and record the activity in the brain of a patient. Electrodes are connected to specific locations of the body from whence they sense minute electrical currents indicative of activity within the brain, and which currents can be used to determine, for example, where and how the brain responds, the extent of the response, and how that response changes over time. Other procedures, such as Computerized Tomographic (CT) scans and Magnetic Resonance Imaging (MRI) are also used to investigate the brain and are often performed on the same patient, which may complicate patient care because most electrodes are incompatible with CT scans and MRIs and cannot remain in place during those procedures.

Neurological monitoring is performed under a variety of circumstances. For example, it may be performed as part of routine testing or by emergency personnel for a victim of a head injury.

Electrodes for neurological monitoring are attached by insertion into or by adhesion to the body of the patient. Accurate placement helps to produce accurate results, and devices exist to improve the accuracy of electrode placement, devices such as harnesses that pinpoint the attachment locations for each of the electrodes. The conditions under which electrode placement is made and the level of experience and training the person performing the electrode placement are relevant to the quality of the measurements subsequently made.

Electrodes are attached to electrical conductors, which are typically thin, insulated copper wires, which carry the signal detected by the electrode to neurological monitoring equipment such as amplifiers and displays. Needle electrodes may be inserted into the body by hand or using devices to release a spring-loaded electrode into the body. Inserting electrodes by hand, and even the use of spring-loaded devices, presents certain risks to the user of "needle stick" injuries.

An electrode that can be quickly and precisely attached to a patient's body, provides good signals, is safe for the patient and the person inserting the electrode and is small enough so as be MRI and CT scan compatible would be an advantage.

SUMMARY OF THE DISCLOSURE

According to the present disclosure, an electrode assembly includes a needle and a thread electrode that is carried by the needle. The needle is inserted into the body and then withdrawn, leaving the thread electrode in place to perform the function of a prior art electrode and an attached electrical conductor. The needle may be secured in a housing in such a way that it may be retracted back within the housing from an extended position in which one end is extended from the housing for the user to insert into the patient's body while it remains attached to a spring inside the housing. A latch is used to move the needle to its extended position against the urging of the spring and to latch it in the extended position for insertion. A protective cover may be applied over the needle while extended and removed just before the needle is inserted into the body of a patient. The thread electrode may be made of a thin conductive material such as non-conductive fibers with a conductive coating.

BRIEF DESCRIPTION OF THE DRAWINGS

In the figures,

FIG. 5A is a detailed cross-sectional view of a portion of a needle showing a groove following the shank of the needle to receive the thread electrode, according to an aspect of the disclosure; and FIG. 5B is a detailed view of a portion of an alternative needle having a slot for holding the thread electrode, according to an aspect of the disclosure.

DETAILED DESCRIPTION

Figure 1:
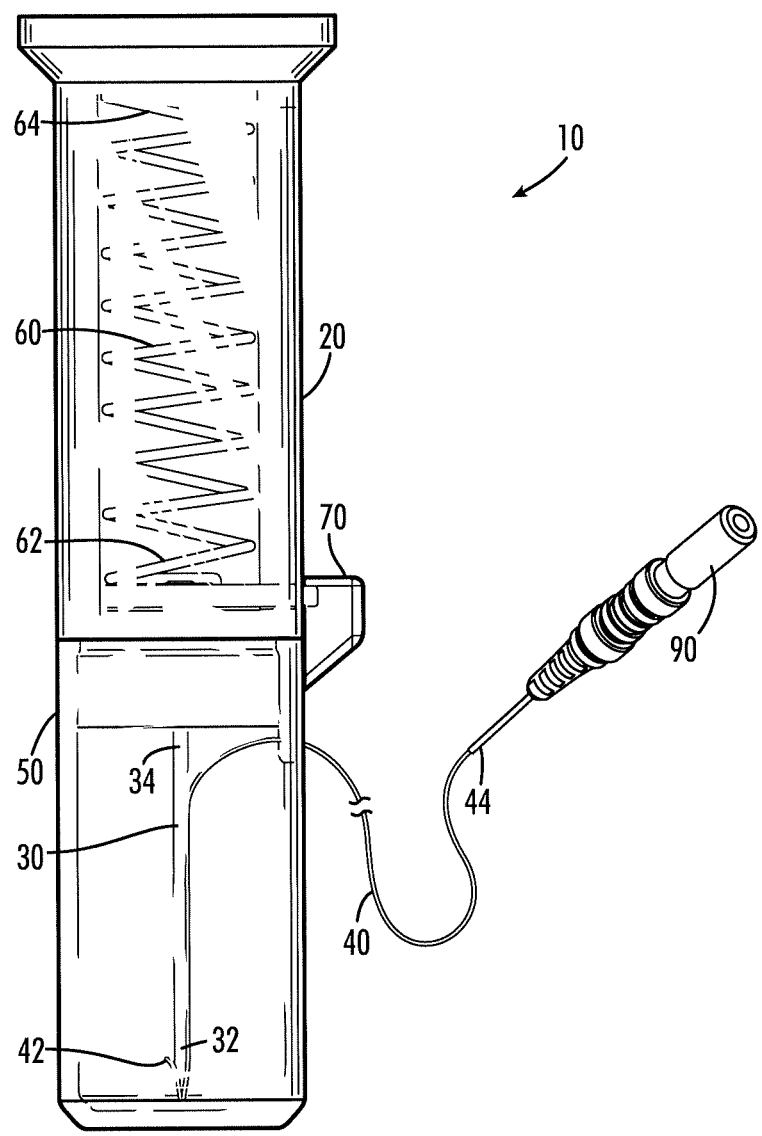
FIG. 1 is an exterior view of the electrode assembly, according to an aspect of the disclosure.

Referring now to FIGS. 1-5B, disclosed herein is an electrode assembly 10 for use in neurological monitoring. Electrode assembly 10 comprises a housing 20, a needle 30, and a thread electrode 40. It may include a protective cover 50, and it may also include a spring 60 and a latch 70.

Figure 2A:
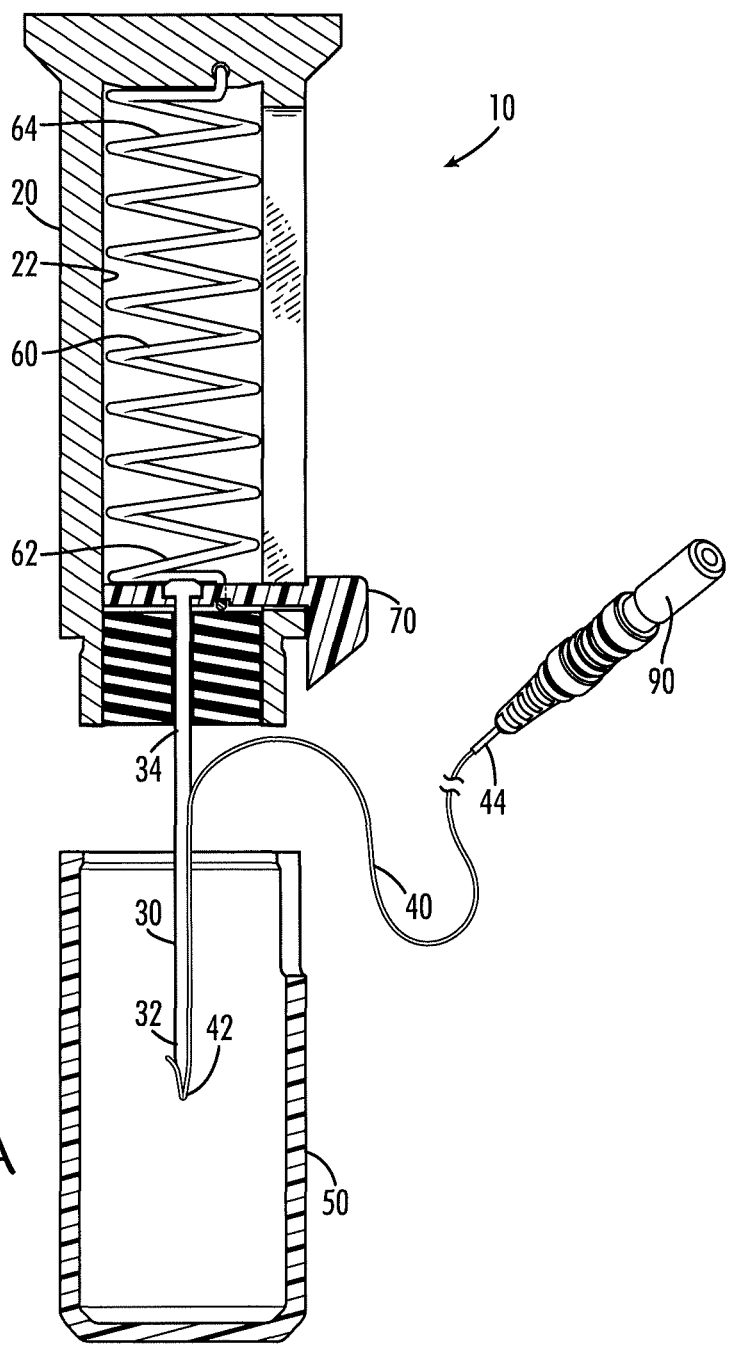
FIG. 2A is a partial cross-sectional, partially exploded view of the housing and protective cover of an electrode assembly, according to an aspect of the disclosure.
Figure 2B:
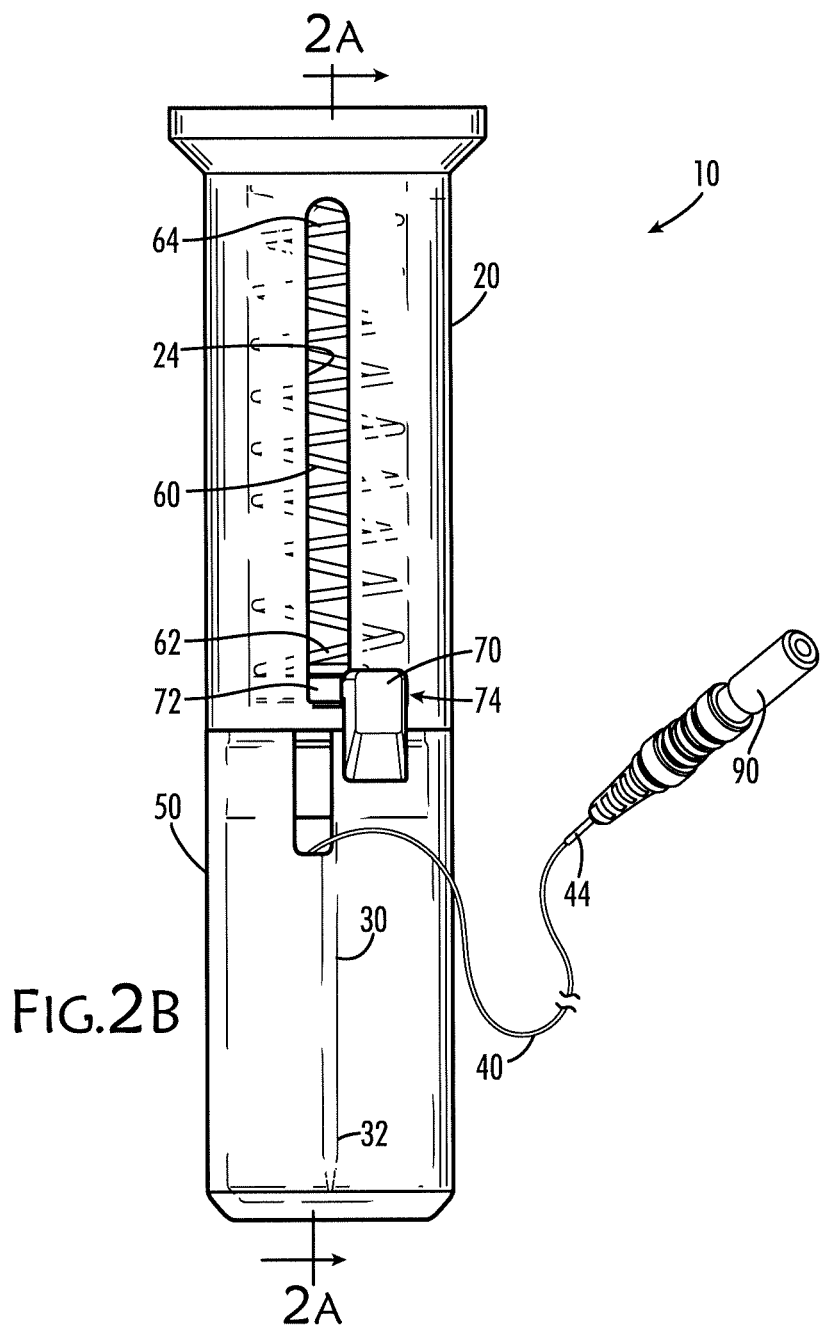
FIG. 2B is the exterior view of the electrode assembly of FIG. 1 rotated about a vertical axis by 90 degrees, according to an aspect of the disclosure.
Figure 2C:
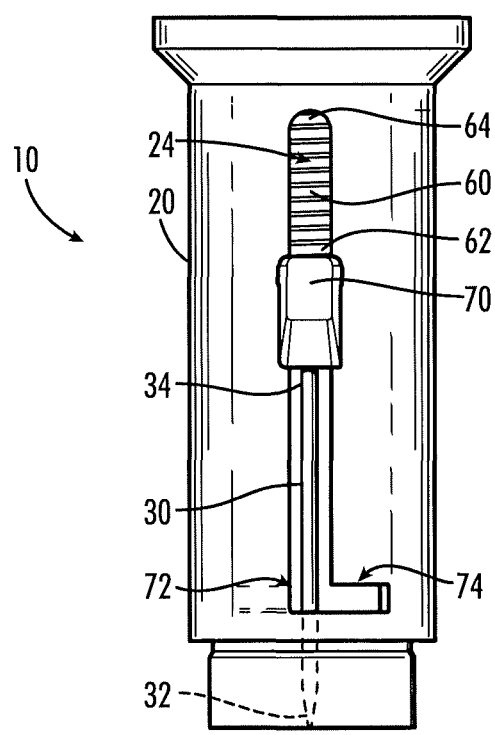
FIG. 2C is an exterior view of the electrode assembly of FIG. 2B with the needle shown in its retracted position and with the protective cover removed, according to an aspect of the disclosure.

Housing 20 is a generally closed container having an interior 22 and may be cylindrical in shape and it has an opening 24. Needle 30 is dimensioned to fit within housing 20 and has a first end 32 and a second end 34. Needle 30 has a retracted position when inside housing 20 and an extended position when needle 30 extends from housing 20 through the opening 24. In the retracted position, as seen in FIG. 2C, first end 32 of needle 30 is positioned in interior 22 of housing 20 and near opening 24 of housing 20, and second end 34 of needle 30 is positioned farther in interior 22 of housing 20 and away from opening 24. When needle 30 is in its extended position, as seen in FIGS. 1 and 2B, first end 32 of needle 30 extends through opening 24 and outside housing 20, and second end 34 is in interior 22 of housing 20. A protective cover 50 fits to housing 20 covering opening 24, and may be used to cover needle 30 when needle 30 is in its extended position, as shown in FIG. 1 and prior to and subsequent to use of needle 30 to deliver thread electrode 40, as shown in FIG. 2A. Protective cover 50 prevents "needle stick" when needle 30 is in its extended position.

Figure 3:
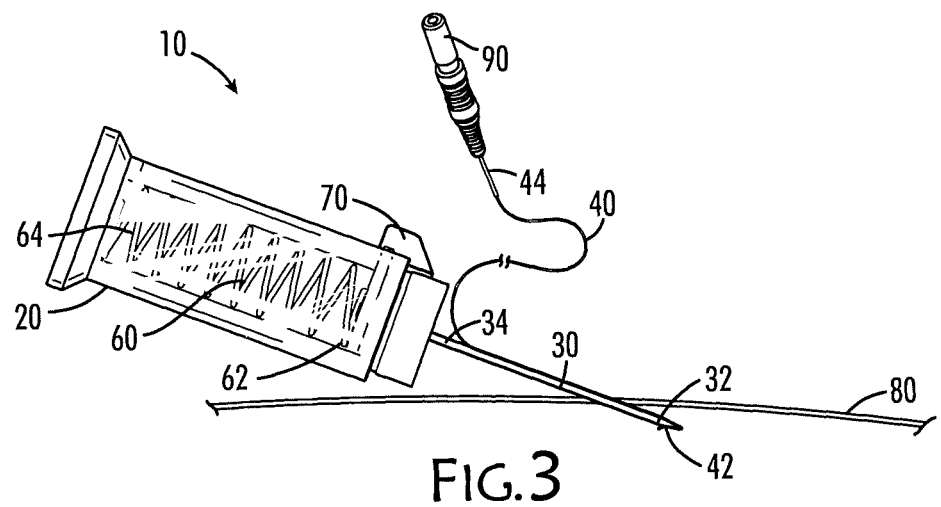
FIG. 3 is an exterior view of the electrode assembly of FIG. 1 with protective cover removed and with the needle and thread electrode extended from the housing and inserted into the body of the patient, according to an aspect of the disclosure.

Thread electrode 40 has a first end 42 and a second end 44. As seen in FIGS. 2A and 3, needle 30 is operable to carry first end 42 of thread electrode 40 when needle 30 moves from its retracted position to its extended position with first end 42 of thread electrode 40 and to yield up or release thread electrode 40 when first end 42 of needle 30 moves to its retracted position from its extended position after penetrating the body 80 of a patient.

Electrode assembly 10 yields up or releases thread electrode 40 into body 80 for use as the electrode and electrical conductor. Thread electrode 40 may comprise a conductive coating over a substrate, and the substrate may be non-conducting, such as a polymer or natural fiber. Thread electrode 40 may be made of thin stainless steel. For example, fibers may be twisted with a stainless steel fiber less than 12 microns in diameter that is very pliable and very strong. Alternatively, natural or synthetic fibers can be coated or electroplated in metals such as aluminum or magnesium. A fiber surface can be softened by heat so that it can capture electrically conductive carbon particles sprayed onto it. Electrically conductive thread electrodes can also be made by embedding conductive metal particles into a non-conductive fiber matrix.

Significantly, a conductive thread made of copper coated substrate uses much less copper than a copper wire, which improves the compatibility of threat electrodes to the effects of CT scans and MRIs.

Electrode assembly 10 may also include a connector 90 attached to second end 44 of thread electrode 40, such as a DIN 42 802 standard connector, which is well-known in neurological monitoring and which enables thread electrode 40 to be connected directly into an amplifier (not shown), for example.

As shown in FIG. 5A, needle 30 may have a groove 36 formed therein dimensioned to receive first end 42 of thread electrode 40. Groove 36 is dimensioned to receive first end 42 and to hold first end 42, when needle 30 carries thread electrode into body 80 by yielding first end 42 on exit from body 80 as the friction and pressure of the inside of the path formed when needle 30 is inserted into body 80 exceeds the resistance applied to first end 42 by groove 36

Alternatively, needle 30 may have a slot 38, as seen in FIG. 5B, formed near first end 32 and which is formed and dimensioned to push thread electrode 40 when needle 30 in inserted into body 80 and yield up thread electrode 40 when needle 30 is removed. Thread electrode 40 placed in slot 38 and is easily driven into body 80 by first end 32 of needle 30 and easily released when needle 30 is removed.

Electrode assembly 10 includes spring 60 secured in interior 22 of housing 20, Spring 60 may be an extension spring and a first end 62 of spring 60 is attached to second end 34 of needle and a second end 64 of spring is attached to housing 20. Spring 60 holds needle 30 in interior 22 of housing 20. Needle 30 may be pulled to its extended position against the urging of spring 60.

Latch 70 is used to pull first end 32 of needle 30 to the extended position and with it first end 62 of spring 60. As shown by comparing FIGS. 2B and 2C, latch 70 has an unlocked position 72 and a locked position 74. Latch 70 may be placed in locked position 74 (FIG. 2B) when needle 30 has been moved to second end 34, and needle 30 will remain there, with spring 60 extended until latch 70 is moved to its unlocked position 72 (FIG. 2C) and released, whereupon needle 30 returns to its retracted position inside housing 20 when urged by spring 60.

Figure 4:
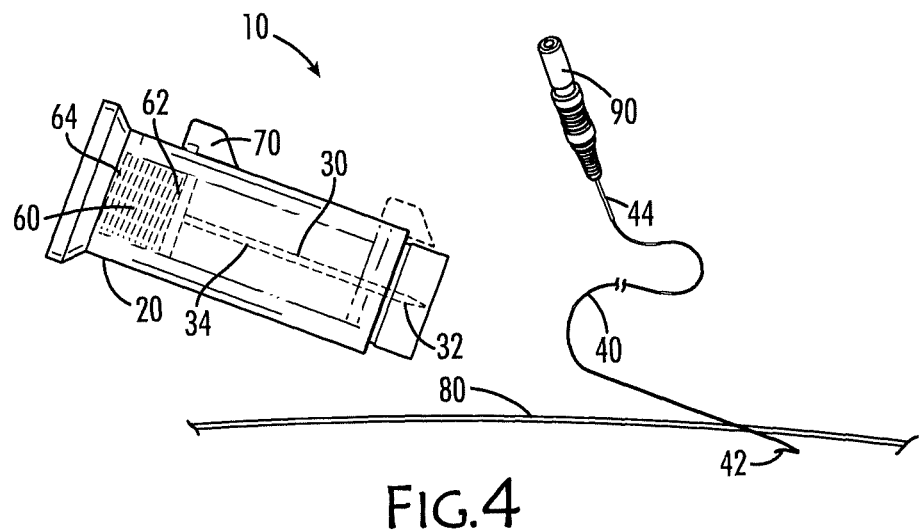
FIG. 4 is an exterior view of the electrode assembly of FIG. 3 with the needle retracted into the housing leaving the thread electrode remaining inserted into the the patient's body, according to an aspect of the disclosure.

When needle 30 is in its extended position as shown in FIG. 1, protective cover 50 is used to guard against needle stick. When needle 30 is to be inserted into body 80, protective cover 50 is removed (see FIGS. 2 and 3) and needle 30 may then be inserted. First end 42 of thread electrode 40 is in position in groove 36 (or slot 38) of first end 42 of needle 30, as best seen in FIGS. 2A and 5A. When needle 30 is in its extended position and latch 70 is in its locked position 74, needle 30 may be inserted into body 80, as shown in FIG. 3. Then latch 70 may then be moved to its unlocked position 72, whereupon spring 60 pulls needle 30 into housing 20 when moving to its retracted position in housing 20, yielding up thread electrode 40 to the body 80 of the patient, as seen in FIG. 4. Thread electrode 40 may easily be removed from the patient's body 80 by pulling thread electrode 40 from body 80.

Those skilled in the use of electrodes for neurological monitoring will appreciate that many modifications and substitutions may be made in the foregoing description without departing from the spirit and scope of the disclosure.

What is claimed is:

1. An electrode assembly, comprising:
a housing having an interior and an opening;
a needle within said housing having a first end and a second end, said needle having a retracted position, wherein said needle is carried in said interior of said housing with said first end of said needle being positioned in said interior and near said opening and said second end being positioned in said interior and away from said opening, and an extended position, wherein said first end of said needle extends through said opening and is outside said housing and said second end of said needle is near said opening and in said interior of said housing; and
a thread electrode carried by said needle having a first end and a second end, wherein said needle is operable to carry said first end of said thread electrode when said needle moves from said retracted position to said extended position and to yield up said thread electrode when said first end of said needle with said first end of said thread electrode has been inserted into the body of a patient and then moves to said retracted position from said extended position.

2. The electrode assembly as in claim 1, further comprising a protective cover connected to said housing and dimensioned to receive said needle and fit to said housing when said needle is in said extended position.

3. The electrode assembly as in claim 1, wherein said thread electrode is a substrate with a conductive coating.

4. The electrode assembly as in claim 3, wherein said substrate is a non-conductive.

5. The electrode assembly as in claim 3, wherein said conductive coating is a metal.

6. The electrode assembly as in claim 1, wherein said thread electrode is a matrix embedded with conductive elements.

7. The electrode assembly as in claim 6, wherein said matrix is non-conductive.

8. The electrode assembly as in claim 1, wherein said thread electrode is made of stainless steel.

9. The electrode assembly as in claim 8, wherein said stainless steel has a diameter of less than 12 microns.

10. The electrode assembly as in claim 1, further comprising a connector attached to said second end of said thread electrode.

11. The electrode assembly as in claim 1, wherein said needle is formed to have a groove therein dimensioned to receive said thread electrode, said thread electrode being carried in said groove.

12. The electrode assembly as in claim 1, wherein said needle is formed to have a slot therein dimensioned to receive said thread electrode, said thread electrode being carried in said slot.

13. The electrode assembly as in claim 1, further comprising a spring secured to said interior of said housing, said spring being attached to said second end of said needle.

14. The electrode assembly as in claim 13, further comprising latch carried by said housing and attached to said second end of said needle, said latch operable to move said needle from said retracted position to said extended position and to hold said needle in said extended position until said latch is released.

* * * * *